United States Patent [19]

Bekesi et al.

[11] Patent Number: 4,666,834
[45] Date of Patent: May 19, 1987

[54] LEUKOCYTE ADHERENCE INHIBITION ASSAY

[75] Inventors: Julius G. Bekesi, Teaneck, N.J.; James F. Holland, Scarsdale; Peter H. Tsang, New York, both of N.Y.

[73] Assignee: Mount Sinai School of Medicine of the City University of New York, New York, N.Y.

[21] Appl. No.: 594,231

[22] Filed: Mar. 28, 1984

Related U.S. Application Data

[62] Division of Ser. No. 285,587, Jul. 21, 1981, Pat. No. 4,455,379.

[51] Int. Cl.$^4$ ............ C12Q 1/02; G01N 33/534
[52] U.S. Cl. ............................. 435/29; 435/2; 435/4; 435/240; 435/241; 435/259; 436/504; 436/804; 424/1.1
[58] Field of Search ............ 436/504, 543, 804, 542, 436/545; 435/2, 7, 259, 272, 1, 29, 240, 241, 267, 268, 820, 212, 4; 424/1.1

[56] References Cited

U.S. PATENT DOCUMENTS

| | | | |
|---|---|---|---|
| 3,999,944 | 12/1976 | Grosser et al. | 424/12 |
| 4,140,753 | 2/1979 | Edgington et al. | 424/1 |
| 4,243,582 | 1/1981 | Spilburg et al. | 260/11 R |
| 4,294,818 | 10/1981 | McMichael et al. | 260/112 B |
| 4,311,686 | 1/1982 | Angers et al. | 424/1 |

OTHER PUBLICATIONS

Hood, L. E. et al., *Immunology*, pp. 91-92, B. Cummings pub., Menlo Park, California (1978).
Zweig, S. E. et al, *Methods in Enzymology*, vol. 92, J. J. Langone et al, ed, Academic Press, N.Y. (1983), pp. 71-72.
Pollack, R., *Readings in Mammalian Cell Culture*, Cold Spring Harbor (1981), see pp. 1-3.
Lowman, J. T. et al, *Radioisotopes in Medicine: In Vitro Studies*, USAEC (1968), R. L. Hayes et al, ed.
Alberts, B. et al, *Molecular Biology of the Cell*, Garland Pub. Co., N.Y. (1983), pp. 160-184.
Price, C. A. in *CRC Handbook of Microbiology*, 2nd ed., vol. IV, pp. 619-658, CRC Press, Florida (1982), A. I. Laskin et al, ed.
Tsang, P. H. et al, J. Immunological Methods, vol. 36, pp. 119-135 (1980).
Eylar, E. H. et al, Methods in Enzymology, vol. XXII, pp. 123-130 (1971).
Cline, G. B. et al, Methods in Enzymology, vol. XXII, pp. 168-204 (1971).
Halliday, W. J. et al, Int. J. Cancer, vol. 9, pp. 477-483 (1972).
Hilfer, S. R. in Tissue Culture Methods and Applications, Kruse, P. F. et al, eds, Academic Press (1973), pp. 16-24, 48.
Journal of Immunological Methods, vol. 31 (12-1979), 259-269, Russo et al.
Journal of Immunological Methods, vol. 33 (4-1980), 323-336, Madsen et al.
Journal of Immunological Methods, vol. 35 (7-1980), 43-56, Biaathen, L. R.
British Journal of Cancer, vol. 29, (1974), 31, Halliday, W. J.
Allergy and Immunology, vol. 26, (2) (1980), pp. 171-178, Varga et al.
Russo A. J. et al, Clinical Research, vol. 26, No. 4, p. 640 (1978).
Shani, A. et al, International Journal of Cancer, vol. 22 (No. 2), pp. 113-119 (1978).

(List continued on next page.)

*Primary Examiner*—Charles F. Warren
*Assistant Examiner*—Margaret Moskowitz
*Attorney, Agent, or Firm*—Brumbaugh, Graves, Donohue & Raymond

[57] ABSTRACT

A new technique is disclosed for assaying for the presence of invasive cancer. While based on leukocyte adherence inhibition, it is improved by using relatively long lived radio-labeled leukocytes, fractionation of the leukocytes to separately treat T-cells and monocytes and by providing for human plasma or serum in the incubation medium.

1 Claim, 8 Drawing Figures

OTHER PUBLICATIONS

Bhatti, R. A. et al, Cancer Research, vol. 39, No. 9, pp. 3328-3331 (1979).

Breborowicz, J. et al, Immunologia Polka, vol. IV, No. 3, pp. 199-207 (1979).

Mortensen, R. F. et al, Journal of Immunology, vol. 124, No. 5, pp. 2316-2323 (1980).

"Radioisotopic $^{51}$ Cr-Leukocyte Adherence Inhibition (LAI) Assay.I. Demonstration of Anti-Tumor Immunity in Patients with Breast Carcinoma", P. H. Tsang, et al., p. 119-135.

"Spontaneous Cytotoxicity of Cultured Human Cell Lines Medicated by Normal Peripheral Blood Lymphocytes", Denis M. Callewaert, et al., 710-717.

"Monocyte Dependence of Pokeweek Mitogen-Induced Differentiation of Immunoglobulin-Secreting Cells from Human Peripheral Blood Mononuclear Cells[1]", Stuart A. Rosenberg, vol. 122, No. 3, 926-931.

"Sensitization of Leukocytes of Cancer Patients Against Fetal Antigens: Leukocyte Migration Studies[1]", vol. 63, No. 2, Aug. 1979, 285-293.

"Antigen-Mediated Macrophage Adherence Inhibition", V. Holan et al., 107-116.

"The L.A.I. Microtest: A Rapid and Sensitive Procedure for the Demonstration of Cell-Mediated Immunity in Vitro", P. G. Holt et al., 277-278.

"Leukocyte Adherence Inhibition as Measured by a Radioisotopic Technique for Detection of Cell-Mediated Tumor Immunity", G. E. Pierce et al, 833-838.

"Historical Background and Aspects of the Mechanism of Leukocyte Adherence Inhibition", W. J. Halliday, 558-563.

"Antigenic Specificity and Cellular Mechanisms in Leukocyte Adherence Inhibition Analysis of Immunity to Simple Proteins and Hapten-Protein Conjugates[1]", Arnold Powell et al., 570-575.

Evaluation of the Microplate Leukocyte Adherence Inhibition Test and Its Reproducibility, Sensitivity, and Relationship to Other Tests of Cellular Immunity[1]", Patrick G. Holt et al., 564-569.

"Tube Leukocyte Adherence Inhibition Assay for the Detection of Anti-Tumour Antigen via Cytophilic Anti-Tumour Antibody", J. H. Marti et al., 48-56.

"Rosette Formation, A Test for Cellular Immunity", J. Wybran et al., 239-245.

"Lymphocytes Bearing Receptors for Both Sheep Erythrocytes and Complement in Patients with Neoplastic and Non-Neoplastic Diseases", Kazimiera J. Gajl-Peczalska et al., 292-299.

"Macrophages and the Tumour Bearing Host", R. Evans, 19-25.

"An Overview: Antitumor Immunity in Breast Cancer Assayed by Tube Leukocyte Adherence Inhibition", M. Flores, MD et al., 494-503.

"Summary and Future Prospects of Leukocyte Adherence Inhibition", Martin H. Goldrosen, 660-662.

"The Natural History of Antitumour Immunity in Human Breast Cancer Assayed by Tube Leucocyte Adherence Inhibition", M. Lopez et al., 1978, 660-672.

LEUKOCYTE ADHERENCE INHIBITION ASSAY

This application is a division of application Ser. No. 285,587, filed on July 21, 1981, now U.S. Pat. No. 4,455,379.

BACKGROUND

Cellular and humoral immune responses against malignant neoplasms are being extensively investigated. Assays of cell-mediated immunity (CMI) fall into thre general categories: tests which measure cell-mediated cytotoxicity (CMC), lymphocyte stimulation (blastogenesis), and lymphokine secretion (migration inhibition). Cytotoxicity and blastogenesis assays require tedious maintenance of aseptic culture conditions and may take several days to complete. Migration inhibition assays, while extremely useful in monitoring CMI responses in cancer patients, take 2 days to perform. Furthermore, there are certain difficulties in their quantification. In search of faster and simpler techniques Halliday and Miller[1] introduced the leukocyte adherence inhibition test (LAI). This 1-day assay was based on their observation that some immune lymphocytes lose their ability to adhere to glass surfaces in the presence of specific tumor antigens. In the original method Halliday incubated mixtures of leukocytes and antigens in hemocytometer chambers. The degree of LAI was determined by counting the residual glass-adherent cells after gentle washing. Subsequent attempts to simplify this technique included Holan's tube method and Holt's microplate method. In the tube method, mixtures were incubated in glass tubes and the non-adherent remaining cells in the fluid were counted in hemocytometers.[2] Holt et al. incubated in plastic tissue culture plates instead.[3] Using these modifications, many workers confirmed Halliday's observation that in addition to cell-mediated reactivities the leukocyte adherence inhibition test can also detect serum blocking factors in patients with advanced stages of neoplasm.

[1] Halliday, W. J. and S. Miller, 1971, *Int. J. Cancer*, 7, 1.
[2] Holan, V. M. Hasek, J. Bubenik and J. Chutna, 1974, *Cell Immunol.* 13, 107.
[3] Holt, P. D., L. M. Roberts, P. J. Fimmel and D. Keast, 1975, *J. Immunol. Methods* 8, 277.

Despite these recent advances, LAI as a method for monitoring cell-mediated immunity in cancer patients still has not been extensively used. One of the main drawbacks is that it requires visual enumeration of adherent (or non-adherent) cells. Several hundred cells in each mixture must be counted to obtain reliable results. When large series of antigens or sera are to be tested, the time factor involved can be critical. This severely limits the number of tests that can be run on the same day. For recent modifications of the assay in which cell enumeration has been automated, elaborate instrumentation is required. In 1974 Pierce and Devald[4] introduced an isotopic variant of the LAI assay by labeling rat lymphocytes with technetium 99m in microplates. Although this approach corrected the imprecision of visual counting the short half-life of $^{99m}$Tc presented some problems since all tests had to be complete in a few hours. The technique was also laborious and difficult to perform.

[4] Pierce and DeVald, *Int. J. Cancer* 14, p. 833 (1979).

These technical difficulties are further compounded by a lack of understanding of the immunological mechanisms by which the response occurs. While most investigators are of the opinion that there is direct interaction of the leukocytes with tumor antigens there is considerable disagreement on the specific cell types and the exact mechanism by which they are involved. Some have contended that inhibition was mediated by a soluble factor released by sensitized lymphocytes in the presence of specific antigen. Alternative mechanisms thought to be operative under certain circumstances include reactions between antigens and cytophilic antibodies on the surfaces of circulating monocytes and the direct action of antigen on sensitized monocytes. These controversies may be attributed to the fact that most of the studies have been performed with poorly characterized leukocyte subpopulations.

THE INVENTION

We have discovered that the sensitivity and selectivity of the LAI assay heretofore described in the art is substantially improved by carrying out this assay as follows:

(a) The blood sample to be assayed is treated to recover leukocytes therefrom. A peripheral blood sample is clinically easiest to obtain and provides leukocytes suit able for assay.

(b) The leukocytes are labeled by a radioactive compound which will either react with or be absorbed by the cell membrane, or penetrate into the intracellular fluids, without substantially affecting cell viability. The compound should be a $\gamma$-emitter and have a half life of at least 5 days. We have found that $^{51}$Cr labeling is particularly suitable for purposes of an LAI assay.

(c) Preferably the radio-labeled leukocytes should be fractionated to separate the T-cells. For reasons which will be explained below, fractionation will also provide for separation of the monocytes. Fractionation of the cells into T-cell and monocyte subpopulations provides improved selectivity, as will be described below. However, it should be understood that our discoveries relating to the use of specially prepared sera or plasma described below, and the use of $^{51}$Cr labeled leukocytes are also applicable to the LAI assay practice without fractionation of the T-cells or monocytes.

(d) The separated or unseparated leukocytes are incubated in an assay dish in the presence of a medium suitable for maintaining cell viability which contains tumor antigen, and which also contains from about 7% to about 20% of a human allogenic blood plasma or blood serum which is antigenically compatible with the patient's red blood cells, and from which complement has been removed or deactivated. Deactivation of the complement can conveniently be accomplished by denaturing.

(e) At the conclusion of the incubation, the non-adherent cells are removed, and the radioactivity of the cells adhering to the assay container is measured. Comparisons between the test sample, incubated in the presence of tumor antigen, and a control sample, in which tumor antigen is omitted during incubation yields an index of leukocyte adherence inhibition.

Using the improved techniques for cell fractionation which will be described herein, we have carried out the foregoing assay using radio-labeled leukocytes which have been fractionated to provide T-cells, B-cells and monocytes of a high degree of homogeneity. This work has demonstrated not only that purified T-cells provide a tumor-specific re sponse in the LAI assay, but that monocytes yield a non-specific reaction to antigens of invasive cancer which will distinguish between patients suffering from such cancer and normal healthy subjects.

An additional companion test which we have developed enables us not only to detect tumor specific response in a patient but also to assay the tumor burden. This further modification is based on the fact that when LAI is applied to leukocytes from a patient having a substantial tumor burden, the patient's own plasma often carries a blocking factor which blocks the normal LAI reaction. By comparing an LAI assay made with allogenic, antigenically compatible serum or plasma in the incubation medium, with an LAI assay in which autologous plasma or serum substituted for allogenic plasma or serum enables the blocking factor to be qualified. This provides an indication of the tumor burden in the patient.

The foregoing assay is characterized by several important aspects:

1. We preferably use $^{51}Cr$ labeled lymphocytes having an intracellular radioactivity of at least $10^4$ counts per minute per $10^5$ cells, or even higher. Such cells are themselves novel, and result from novel methods of labeling hereinafter described.

2. A novel 2-stage procedure hereinafter described is used to isolate lymphocyte subpopulations from pre-labeled leukocytes. Each of the isolated fractions, i.e. T- and B-lymphocytes and monocytes, were found to be highly homogeneous as monitored by surface markers, morphological parameters and by mitogen responses. Viability, incorporation and level of spontaneous release of $^{51}Cr$ in all fractions are not affected by the purification procedures. This process enables highly purified radioisotope-labeled leukocyte subpopulations to be applied in an LAI assay to diagnose and monitor specifically the presence of malignant neoplasms in tested subjects.

3. We found that the inclusion of normal human allogenic plasma or serum antigenically compatible with the patient's red blood cells, and freed from complement, prevents non-specific LAI responses to unrelated tumor antigens. AB plasma or serum is convenient, and is preferred. Such non-specific reactions have been a common problem with earlier LAI assays. We have found that best results are obtained when the serum comprises about 7%–20% (by volume) of the incubation mixture. Preferably, we use a concentration of about 10%.

In addition, compared to other methods the $^{51}Cr$ LAI assay is more accurate, more precise, less laborious, less time-consuming and more objective. Furthermore, the entire population of leukocytes, or the T- or B-lymphocyte, or monocyte subpopulations can be analyzed instead of small samples chosen at random from a microscopic field. These considerations qualify our invention as a unique and useful tool in detection of neoplastic growth, response of the cancer patients to treatment and to study the host immune response. Our findings are summarized as follows:

1. We have established that the reactive cells that undergo reduced adherence as a specific response to related tumor antigen are T-lymphocytes. Our results show the B-lymphocytes from cancer patients are non-reactive to tumor antigens in LAI. Monocytes, on the other hand, respond non-selectively to an array of tumor antigens but not to normal tissue antigens. Compared to unseparated $^{51}Cr$ labeled leukocytes, T-lymphocytes reflect the LAI reactivity of cancer patients with higher frequency and remarkable specificity. In clinical studies, we were able to distinguish between groups of patients with invasive cancer and those with benign disease with a high degree of reliability.

2. Among normal subjects, T-lymphocytes were unreactive to tumor antigens. Non-specific LAI response was detected with monocytes against tumor antigens although the level of reactivity was uniformly lower than that observed in sensitized monocytes isolated from cancer patients. We speculate that these non-specific LAI responses are directed by both sensitized and non-sensitized monocytes towards a surface antigen common to all neoplastic cells.

3. On substituting normal allogenic plasma with the patients' autologous plasma we found specific blocking factors in almost all patients with advanced tumor. These serum blocking factors were able to abrogate specific recognition of T-lymphocytes to the related tumor antigen.

This invention will be better understood from the attached Figures in which:

FIG. 1 outlines the manner in which antigens are prepared for an LAI assay in accordance with the present invention.

FIG. 2 outlines the procedure for isolating, characterizing and labeling peripheral blood leukocytes for use in the present invention.

FIG. 3 outlines the procedure for the isolation of leukocyte subpopulations.

FIG. 4 outlines the basic steps of the leukocyte adherence inhibition assay of the present invention.

FIG. 5 shows the leukocyte adherence inhibition measured in accordance with the present invention of the various subpopulations of leukocytes FIGS. 6, 7 and 8 show the results of various tests conducted with the leukocyte adherence inhibition of the present invention.

DETAILED DESCRIPTION OF THE INVENTION

Antigen for use in the present invention can be prepared in any of the usual ways previously described with respect to the LAI assay. However, we prefer to use a special technique which we have found to provide antigen of plasma membrane origin with fewer contaminants of other cell material.

Figure 1:
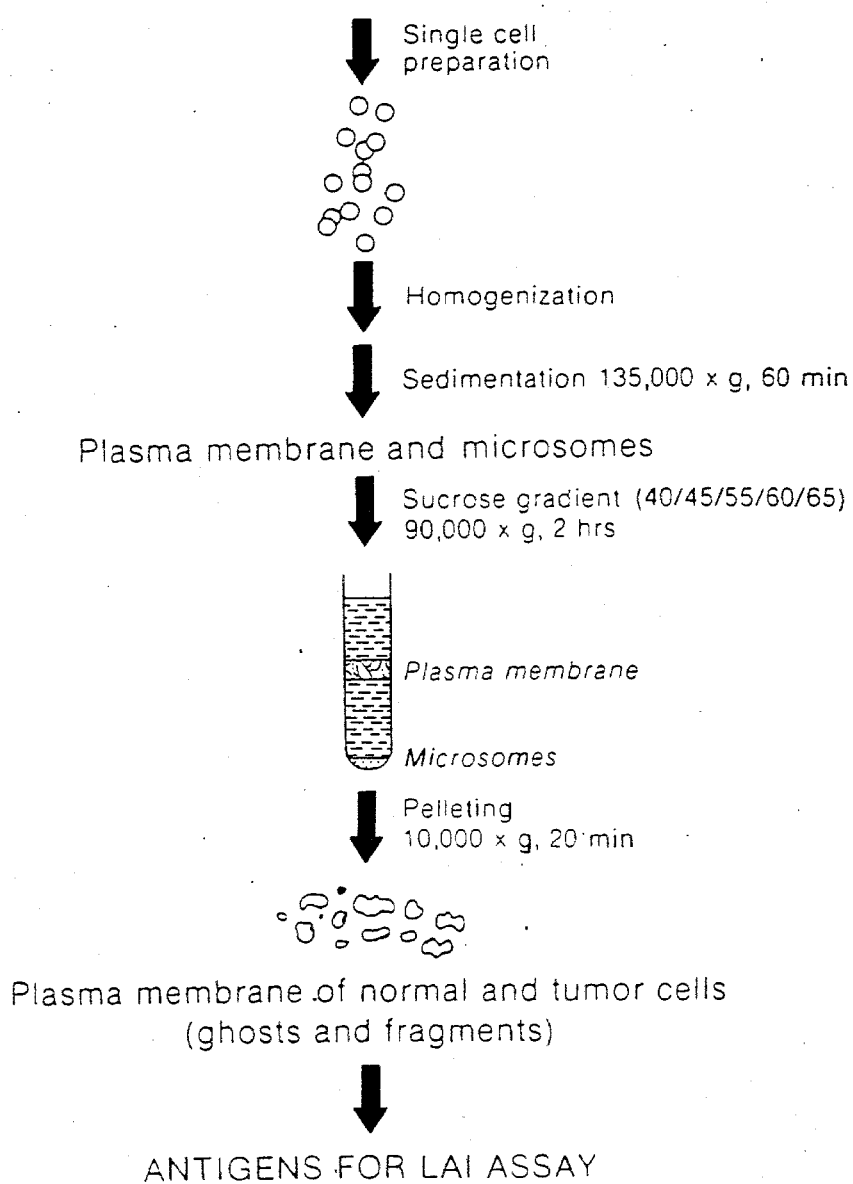

FIG. 1 outlines the novel preferred method for preparing antigen for an LAI assay. While developed for and applicable to the assay procedure of the present invention, the method described below is, of course, applicable to the other LAI assay procedures.

The first step in our procedure to prepare a single cell suspension of the malignancy by cutting surgically removed specimens of the malignancy to be used as the antigen source into small pieces and treating it with a proteolytic enzyme effective to digest connective tissues. This results in a suspension of single cells which can be removed by aspiration after sedimentation of the disrupted tissues. We have found that collagenase is particularly suitable for use in the digestion step. Ordinarily, digestion is carried out for a period of approximately 15 minutes under the conventional conditions using mild agitation. Such a preparation is required for each different histological origin of malignancy tumor to be assayed, i.e. breast cancer, mesothelioma, melanoma, colorectal cancer, lung cancer, pancreatic cancer, leukemia and others.

The single cell preparation is then washed to remove excess enzymes and homogenized mechanically to break the cell membrane. This may be accomplished for example by treating the single cell suspension in an ice-cooled nitrogen cavitation bomb at a pressure of 30 atmospheres for 15 minutes. Sudden decompression causes cell explosion. The suspension of broken cells released in the bomb is centrifuged under conditions effective to remove intact cells, cell nuclei and mitochondia.

Plasma membrane microsomes and lysosomes in the supernatant are collected and recentrifuged on a discontinuous sucrose gradient (for instance, having concentrations ranging from 40% to 60%) to separate plasma membrane from the microsomes and lysosomes. Removal of plasma membranes from lysosomes is important inasmuch as lysosomes release hydrolytic enzymes, which, if not removed, tend to digest the plasma membrane. Centrifugation at $90,000 \times g$ for 2 hours is sufficient to achieve this separation. The interfacial band containing plasma membrane particulates was collected, washed twice, its protein content determined, and adjusted to give final protein concentration of 2-5 mg per ml of 20% sucrose. This preparation is designated as "tumor antigen" in LAI assay procedures, as will be so referred to hereinafter.

Experience has shown that not all tumor antigen preparation has the capacity to evoke tumor specific response. Accordingly, the tumor antigen is tested for activity and cross-reactivity using an LAI assay, such as in accordance with the present invention, to determine whether the candidate antigen tumor, when incubated with leukocytes from patients known to have a malignancy of the same histological origin and patients known to be free of such a malignancy, bring about a tumor-specific inhibition of leukocyte adherence. Those antigen preparations demonstrated to be active and having a tumor-specific response are then stored at $-196°$ C. for use in assays in accordance with the present invention. After thawing, antigen preparations were always centrifuged at $2000 \times g$ for 10 minutes before being used.

Figure 2:
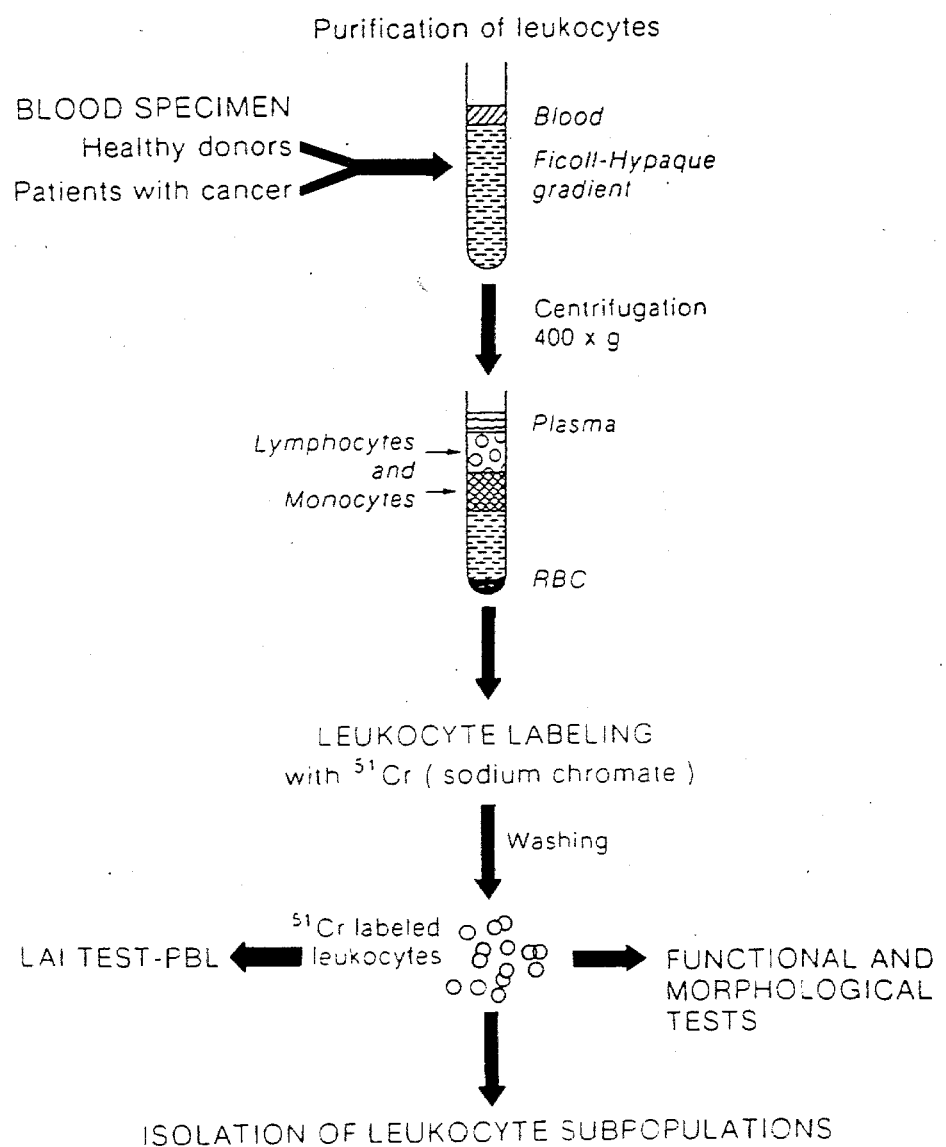

FIG. 2 outlines the procedure for the preparation of peripheral blood leukocytes (PBL) for the LAI test. Heparinized blood specimens are drawn from the patient to be tested and the blood is fractionated to separate lymphocytes and monocytes. The fraction containing lymphocytes and monocytes is recovered for radio-labeling with $^{51}Cr$ sodium chromate. Preferably a sample of unlabeled leukocytes are also characterized for T-lymphocyte, B-lymphocyte and monocyte population and for viability. Viability is important in as much as successful completion of the test procedure requires viable lymphocytes and monocytes.

$^{51}Cr$ labeling should be effective to produce a labeled leukocyte population having intracellular radioactivity of at least $10^4$ cpm per $10^5$ PBL, and characterization of the labeled leukocytes should indicate that the T-lymphocyte, B-lymphocyte and monocyte populations, viability and functionally are all substantially similar to the initial leukocyte fraction.

It will be appreciated that leukocytes which have been labeled under less than the preferred conditions, and having an intracellular radioactivity of less than $10^4$ cpm per $10^5$ leukocytes, can be used. Such a lower radioactivity, however, increases the counting time for completion of the test and can disproportionately reduce sensitivity.

While it has been known that media such as RPMI-1640, physiological saline and, physiological saline plus glucose can be used in radio-labeled leukocyte with $^{51}Cr$, we have found, that as a rule these media generally do not yield a labeled leukocyte population with sufficient radioactivity for the preferred practice of the present invention. To obtain improved yields of radioactivity we have found that the incubation medium should also contain from 1-6 gm/liter of potassium chloride as well as a physiologically acceptable concentration of sodium chloride and a nutrient sugar, such as glucose or dextrose (hereinafter GNK). We have successfully used media containing 0.9% sodium chloride plus 2 g/l KCl plus 1 g/l dextrose, 0.9% sodium chloride plus 4 g/l KCl plus 1 g/l dextrose (optimal medium), and 0.9% sodium chloride plus 6 g/l KCl plus 1 g/l dextrose.

Upon suspending the leukocytes recovered from the patient in an appropriate medium, such as the optimal medium mentioned above, sodium chromate is added to provide at least 150 $\mu$Ci of $^{51}Cr$. The mixture is then incubated for a suitable period of time typically one to two hours at 37° C. sufficient for the PBL to take up $^{51}Cr$ in an amount sufficient that the labeled cells will exhibit an intracellular radioactivity of at least $10^4$ counts per minute per $10^5$ cells. After incubation, the tubes are removed and rapidly cooled by ice water. The mixture is centrifuged to separate the labeled PBL, which are washed to remove extracellular $^{51}Cr$. The washed leukocytes are then stored in a suitable medium such as RPMI-1640 for further use in accordance with the LAI assay of the present invention and for further separation.

The traditional procedures for separating T-lymphocytes, B-lymphocytes and monocytes involve a two-step procedure in which the monocytes are first caused to take up an extraneous heavy element such as iron, which permits them to be separated by centrifugation. Thereafter, the remaining lymphocytes are treated with sheep red blood cells (SRBC) which form rosettes with the T-lymphocytes and enable recovery of the T-lymphocytes by centrifugation. T-lymphocytes are removed from the SRBC by lysing the sheep and blood cells.

We have discovered a new procedure for separating T-cells, B-cells and monocytes which improves on the traditional technique since our procedure enables the monocytes to be recovered in viable form. Our preferred procedure for separating T- and B-lymphocytes and monocytes is outlined in FIG. 3. In the initial stage, the leukocyte suspension is treated with SRBC, which form rosettes with T-lymphocytes which are thereupon removed by centrifugation. Since this rosetting does not normally result in bonding between the sheep red blood and T-cells strong enough to withstand a high-gravity centrifugation, the efficiency of T-cell recovery can be poor. We have improved on this procedure by first treating the sheep red blood cells with a halogenating reagent which causes halogen ions to become attached to the SRBC. Upon treating the leukocytes mixture with the halogenated SRBC, the halogen forms an additional ionic linkage with the T-cells which improves the strength of the rosette formation. In this manner, the efficiency of rosette recovery under centrifugation is vastly improved.

The halogenating reagent used in the present invention comprises a carrier ion and a negative halogen ion, preferably bromine. The carrier ion must be physiologically innocuous with respect to both the sheep red blood cells and the lymphocytes, and must be capable of giving up the halogen ion which it carries when brought in contact with the sheep red blood cells. We have found an amino alkyl thiouronium halide such as amino ethyl isothiouronium bromide (AET) from the Sigma Company of St Louis to be particularly suitable.

In accordance with the present invention, AET-treated SRBC (0.5 gm AET per 10 ml SRBC treated for 15 minutes at SRBC) were mixed with labeled cells in a ratio of 100:1 in RPMI-1640 containing 20% SRBC-absorbed FCS. The suspension was then incubated at 37° C. for 5 minutes, spun at 200×g for 5 minutes and incubated at 4° C. for 1 hour. The suspension cells were then layered on Ficoll-hypaque and the rosettes pelleted at 400×g for 40 minutes. The SRBC in the pellet was immune-lysed with autologous plasma at 37° C. for 15 minutes and the T-lymphocytes washed with medium RPMI-1640. The non-rosetting fraction at the interface, enriched in B cells, null cells and monocytes was also collected.

After separating the T-cells by rosetting and centrifugation, the supernatant liquid remaining contains monocytes and B-cells. Our procedure then provides for separation of the monocytes and B-cells by means of a density gradient and centrifugation under conditions effective to take advantage of the density differences between monocytes and B-cells. Preferably, we employ a discontinuous Percoll density gradient. Percoll, a modified colloidal silica, was purchased from Pharmacia (Piscataway, N.J.). Nine volumes of Percoll were diluted with 1 volume of 1.5M NaCl to make up a stock solution of isotonic Percoll of density 1.124 g/ml, pH 8.4. The mononuclear band from F-H centrifugation according to step 1 was diluted to 7 ml with 0.15M NaCl and layered on top of 3 ml of a 50% (v/v) solution of isotonic Percoll in 0.15M NaCl. A second centrifugation for 60 minutes at 800×g at 4° C. produced an interfacial band which contained monocytes and a bottom layer which contained non-E-rosetting lymphocytes (B-lymphocytes and null cells). Monocytes were collected and set aside. The B-lymphocytes with receptors for complement $C_3$ were isolated from the bottom layer by the EAC rosetting method. Sheep RBC sensitized with rabbit IgG anti-SRBC and human complement $C_3$ (EAC) were obtained from Cordis Biological. The rosetting procedure was performed by mixing EAC and the non-E-rosetting lymphocytes in a ratio of 100:1 in RPMI containing 20% SRBC-absorbed FCS. The rosettes thus formed were incubated for 5 minutes at 37° C. and sedimented at 200×g. After 1 hour incubation at 37° C., the rosettes were resuspended, layered on Ficoll-hypaque and pelleted at 400×g for 40 minutes. The SRBC in the pellet was lysed with $NH_4Cl$ buffer and the B lymphocyte washed twice with medium RPMI-1640.

Figure 4:
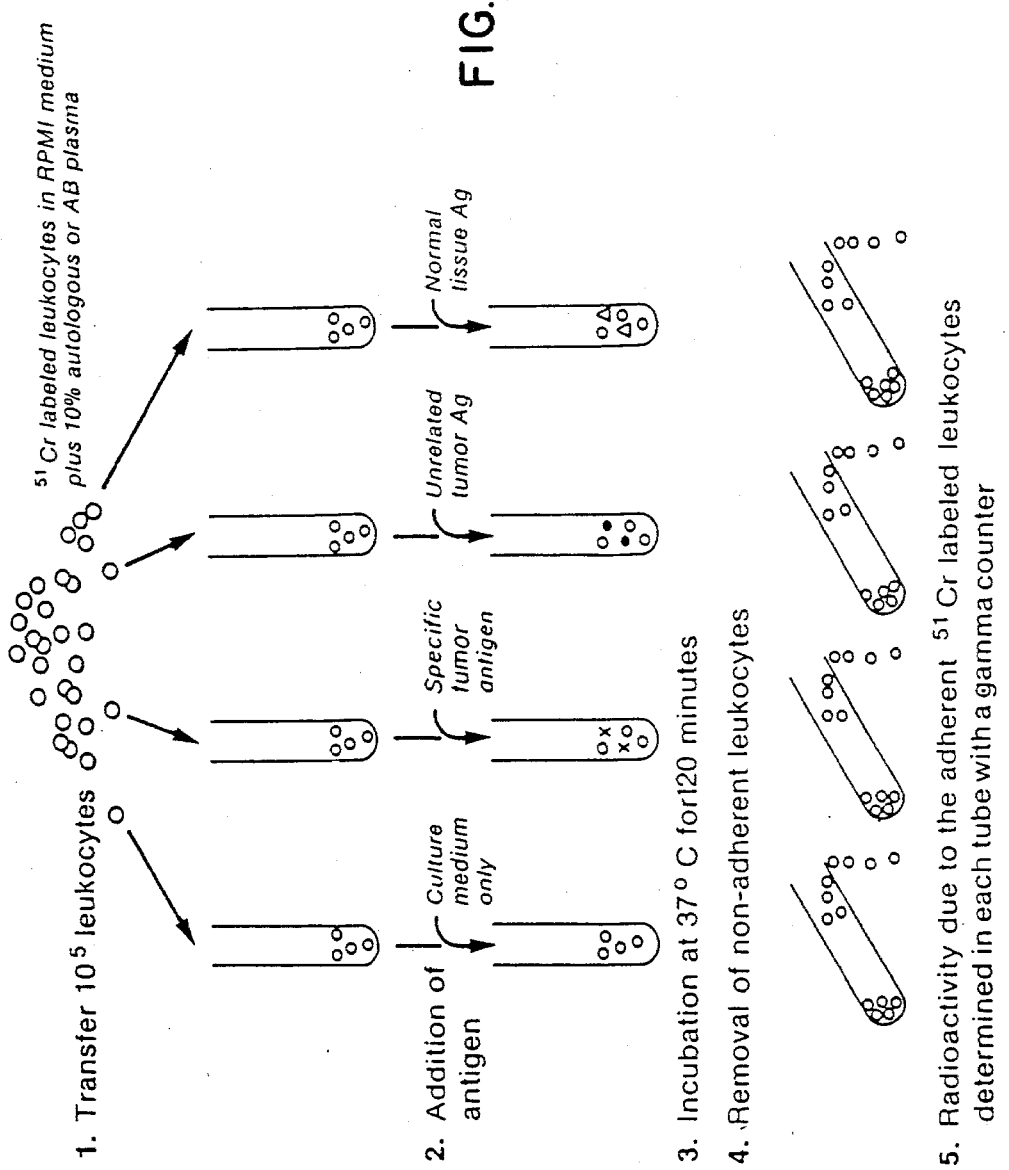

Referring to FIG. 4, the procedure for assay is outlined. $^{51}Cr$ labeled PBL, T-, B-lymphocytes or monocytes in the storage medium plus 10% autologous serum or AB plasma are transferred to an appropriate culture container for carrying out the assay. Any convenient number of leukocytes may be transferred so long as the number transferred to each culture container does not exceed that which would form a monolayer if complete plating on the culture dish occurred. Typically, we employ considerably less than this number of leukocytes in relation to the size of the culture dish. For instance, when employing 13 mm×100 mm culture tubes of glass or polyethylene, we find it convenient to prepare the leukocytes in a concentration of $1 \times 10^5$ to $1 \times 10^7$ cells/ml, and to transfer aliquots, each containing between $10^4$ and $10^6$ leukocytes, to each culture container.

In the second step, tumor antigen from the same histological origin of the suspected malignancy is added to one of the culture containers. Another culture container is used as a control which has been seeded with $^{51}Cr$ PBL and incubated without addition of tumor antigen. Additional controls may be employed if desired. For example, as an additional control, a sample of leukocytes or a leukocyte subpopulation to be assayed may be incubated with an unrelated tumor antigen or a sample may be incubated against tissue antigen from normal organs.

Incubation is continued under conditions (time, temperature, atmosphere) sufficient for a significant portion of the leukocytes in the control culture dish to plate out onto the surface thereof. Typically, such incubation will continue in the order of 1-3 hours at 37° C. At the conclusion of the incubation period the suspension of non-adhering leukocytes is removed and the culture container is washed to remove any non-adherent leukocytes remaining. After drying, the radioactivity of the adherent $^{51}Cr$ PBL in each sample is counted. Spontaneous release of 20-25% of the incorporated radioactivity from labeled lymphocytes was observed during the performance of the LAI assay. As described above, this was monitored by assaying radioactivity of the supernatant, after centrifuging, in 1 out of 4 tubes. These data were taken into account in the calculations of LAI by subtracting the background value of spontaneous release from the total observed value of radioactivity. The net radioactivity represents the corrected experimental value under the conditions employed. Results are evaluated by the LAI index calculated by the formula:

$$LAI = \frac{A - B}{A}$$

where

A=mean cpm of adherent cells without antigen after correction for spontaneous release, and B=mean cpm of adherent cells with antigen after correction for spontaneous release.

The present invention is further illustrated by the following clinical tests of the procedure:

Materials and Methods (A) Subjects Tested

Blood samples were drawn preoperatively from 48 previously untreated women (age 25-73, mean age 56.5 years) with suspected breast carcinoma or benign breast disease. Diagnosis was confirmed within a few days by histological examination of biopsy specimens. A confirmed pathologic diagnosis was not available at the time of assay and the test was conducted without knowledge of the diagnosis. Control samples from 32 apparently healthy, age-matched (24-59, mean age 49.6 years) female donors were obtained from the blood bank. In addition, 15 patients of both sexes with acute myelocytic leukemia in clinical remission were also studied.

(B) Collection of Blood Samples for Lymphocyte Studies

Peripheral blood was drawn in a heparinized (10 units of preservative-free heparin/ml blood) plastic syringe. Lymphocytes were isolated on a Ficoll-Hypaque gradient (Pharmacia Fine Chemicals) and centrifuged for 30 min at 1000×g at 20° C. The mononuclear cells located at the interface of the gradient were collected, washed 3 times with phosphate-buffered saline (PBS) and resuspended at a concentration of $2 \times 10^7$ cells/ml of glucose-saline solution (GNK) containing 1 g dextrose, 4 g potassium chloride and 9 g sodium chloride per liter of triple distilled water, pH adjusted to 7.4. Viability of lymphocytes was 98–100% as measured by vital dye exclusion using trypan blue.

(C) Quantification of PBL Subpopulations (i) T-Lymphocytes

The percentage of T-cells was enumerated by the E-rosette formation assay[5] (Wybrad, 1971). Two ml of sheep erythrocytes (E) suspended in an equivalent volume of Alsever's solution (obtained fresh bi-weekly from Cordis, Miami) were placed in a 50 ml centrifuge tube, diluted to 50 ml with RPMI-1640 to give $1 \times 10^8$ cells/ml. Heat-inactivated fetal calf serum (FCS, Gibco) from a single lot was repeatedly absorbed with packed E at 3:1 ratio for 2 minutes at 37° C. and for a further 30 minutes at 4° C. before being frozen in small aliquots. 0.2 ml of absorbed FCS was added to 0.1 ml of PBL suspension ($2 \times 10^6$ cells/ml) in $12 \times 75$ mm disposable glass tubes (Fisher Scientific). 0.2 ml of the E suspension was then added and the tubes containing PBL and E were incubated for 5 minutes in a 37° C. incubator. After incubation, they were centrifuged at 200 g for 5 minutes at 20° C. and kept overnight at 4° C. Prior to quantification of E-rosette forming PBL, the cells were gently resuspended. Lymphocytes were stained with a drop of 0.2% toluidine blue (Fisher Scientific) and placed in a hemocytometer to be counted. The percentage of E-rosette forming lymphocytes (E-RFC) was determined by first counting the rosettes and then the lymphocytes not engaged in rosette formation. A lymphocyte with 3 or more erythrocytes firmly bound to its surface was termed a E-RFC. The percentage of E-RFC was calculated from a count of 100 lymphocytes.

[5] Wybrad J. and Fundenberg, *Trans. Assoc. Am. Physicians* 84, p. 239 (1976).

(ii) B-lymphocytes

B-cells with receptors for complement $C_3$ were detected by EAC rosette method. Sheep RBC sensitized with rabbit IgG anti-SRBC and human complement $C_3$ (EAC) were obtained from Cordis Biological. The rosette assay was performed by mixing equal volumes (0.1 ml) of EAC and PBL, incubating the mixture for 5 minutes at 37° C. and sedimenting the mixture for 5 minutes at 200 g. Rosettes were scored as described after 1 hour incubation at 37° C.

(iii) Monocytes

Monocytes were identified by both the peroxidase histochemical stain[6] and by the latex-ingestion technique[7]. In the staining method, smears were prepared from pelleted cells and were fixed for 3 minutes in an ethanol solution, (0.25 g benzidine, 0.5 g sodium nitroprussiate, 96% ethanol, total volume 100 ml) rinsed and covered with the ethanol solution mixed with 2 drops of 3% hydrogen peroxide solution for an additional 5 minutes. Slides were then washed with PBS (pH 7.2), dried and mounted in glycerol buffer. Monocytes were stained light blue.

[6] Kazimiera et al., *Clinical Immunology and Immunopathology* 8, p. 292 (1977).
[7] Evans, *Br. J. Cancer* 28, Suppl. I, p. 19 (1973).

Alternatively, cell suspensions ($2 \times 10$/ml) were incubated in 1 ml RPMI-1640 containing 20% FCS with 5 µl of uniform Latex particles (2 µm in diameter, supplied by Dow Chem., Indianapolis, Ind.). Incubation was at 37° C. in a shaking waterbath (Fisher Scientific) for 60 minutes. Cells were then washed gently at $300 \times g$ with PBS, stained with Wright-Giemsa stain (Fisher-Scientific) and examined microscopically for ingested latex particles by phagocytic cells.

(D) Sera

Autologous serum was obtained from each subject by allowing the blood to coagulate. It was centrifuged at $400 \times g$ for 20 min within 2 h. Human AB pooled serum was obtained from North American Biological Inc. Fetal calf serum from Microbiological Ass. and human serum albumin from Pharmacia Fine Chemicals were also utilized in certain studies discussed below. Complement present in these sera was denatured by heating the sera at 56° C. for 1 hr before use.

(E) Leukocyte Labeling $^{51}Cr$ sodium chromate with specific activity of 350–500 µCI/ug (New England Nuclear, Boston Mass.) was used throughout this study. Purified peripheral blood leukocytes were suspended in polyallomer tubes (Beckman) in a medium containing a nutrient sugar such as glucose or dextrose (1 g/l), sodium chloride (9 g/l), and 4 g/l potassium chloride (GNK). The final lymphocyte concentration was $0.5-2 \times 10^7$ cells/ml. Incubation was carried out in the presence of 200 µCi of $^{51}Cr$ in a Dubnoff water bath at 37° C. while shaking at the rate of 100 c/min for 45 min. After incubation, the tubes were removed, rapidly cooled by adding 30 ml of ice-cold GNK, mixed and centrifuged at $400 \times g$ for 10 min at 4° C. Labeled lymphocytes were washed 3 times with 40 ml ice-cold GNK as above and resuspended to a final concentration of $1 \times 10$ cells/ml in RPMI-1640+AB serum of RPMI-1640+autologous serum. At that point, the total incorporation of $^{51}Cr$ into PBL was determined by transferring $10^5$ lymphocytes to counting tubes for counting in a thallium-activated sodium iodide well-type gamma counter (Packard Instruments).

Microscopic examination of PBL before and after labeling with $^{51}Cr$ showed only slight changes in subpopulation of lymphocytes. After chromation, the average number of T-cells was 68.2%, of B-cells 18.3% and of monocytes 16.2%. Identical values were obtained when the PBL were incubated under the same experimental conditions with $^{51}Cr$ omitted.

(F) Isolation of PBL Subpopulation

A novel two-stage procedure was used to isolate enriched cell fractions from pre-labeled PBL of normal and tumor bearing subjects. The percentage of T-, B-cells, and monocytes in each cell fraction was monitored by surface markers and phagocytic monocytes were identified by ingestion of latex particles and by histologic stains for peroxidase. The experimental protocol for isolation of these various PBL subpopulations is summarized schematically in FIG. 4. Results in Table I show that after the isolation rosetting subpopulations contained 93±3% T-lymphocytes, virtually no $C_3$ receptor positive cells (B cells) and no phagocytic monocytes (<1%) and 1 to 6% null cells (cells with no E or C receptors). The non-E-rosetting fraction at the interface of the Ficoll gradient, on the other hand, was depleted of T-cells and enriched in B-cells, monocytes and null cells. Monocytes were selectively removed from this mixture by Percoll gradient centrifugation. The interfacial band consisted almost exclusively of phagocytic monocytes (92.3%). The B-lymphocytes fraction isolated by EAC rosetting method from the remaining cellular mixture contained about 85% $C_3$ receptor positive cells.

TABLE I

SURFACE MARKERS OF ISOLATED PBL SUBPOPULATIONS

| Cell Subpopulations | Percent Of Cells Positive For | | | |
|---|---|---|---|---|
| | E-Rosettes (Range) | $C_3$-Receptors (Range) | Phagocytosis (Range) | Peroxidase (Range) |
| Unseparated | 68.2 ± 6 (60–71%) | 8.3 ± 3 (9–15%) | 16.2 ± 4 (16–21%) | 19.1 ± 4 (1.7–23%) |
| Enriched T-cells | 93.2 ± 3 (90–96%) | 1% | 1% | 2% |
| Enriched B-cells | 6.3 + 3 (5–10%) | 85.2 + 5 (81–88%) | 1% | 2% |
| Enriched Monocytes | 1% | 1% | 92.3 ± 4 (88–95%) | 91.1 ± 5 (89–94%) |

A relatively good yield was obtained in each separation step. On subjecting $100 \times 10^6$ labeled PBL to E rosette sedimentation, close to $63 \times 10^6$ rosette forming cells were recovered in the T-cell fraction while $30 \times 10^6$ non-rosetting cells were retrieved from the Ficoll-Hypaque interface. This cellular mixture of B-cells, null cells and monocytes, when applied onto a Percoll density gradient, yielded $12 \times 10^6$ phagocytic cells. The final yield of B-lymphocytes, isolated by the EAC rosetting technique was $14 \times 10^6$ cells Thus the total yield from the separation techniques was 92.6%, 77.8% and 75.1% for T-cells, B-cells and monocytes respectively. All of the populations had a viability of about 98% after separation.

(G) Monitoring of Function of PBL Subpopulations by Blastogenesis Assay

The various PBL subpopulations were assessed functionally by their response to synthetic mitogens, PHA, Con A and PWM. Human peripheral blood T-lymphocytes, but not B-lymphocytes, are activated by PHA and Con A to proliferate. By utilizing this specificity, one can determine how pure the separated cell populations were. Isolated subpopulations of T-cells, B-cells and monocytes were cultured in microtiter plates at a concentration of $1 \times 10^5$ viable cells per well in 200 μl of medium RPMI-1640 containing 10% autologous serum in an atmosphere of 5% $CO_2$. 0.3 μg of PHA (Microbiol. Assoc., Bethesda, Md.) and 5 μg of Con A (Microbiol. Assoc., Bethesda, Md.) were added in triplicate to each of the wells. After two days of incubation, 0.5 μCi of $^3H$ thymidine (New England Nuclear, Boston, Mass ) was added to each of the wells and the cells cultured for an additional 24 hours. Cells were then harvested using a multiple automated sample harvester (Microbicl Assoc., Bethesda, Md.).

Proliferation was assessed by the degree of thymidine uptake as measured in a liquid scintillation counter (Packard, Downers Grove, Ill.) T-lymphocyte enriched fractions showed enhanced reactivity to the T-cell mitogen PHA (50% increase) and Con A (33% increase) as compared to the unseparated cells. Conversely, the B-enriched populations had a minimal response to both the T-cell mitogens, thus indicative of the reduction in numbers of functionally reactive T-cells. Monocytes, as expected, were essentially non-reactive to either mitogens (Table II).

TABLE II

FUNCTIONAL CHARACTERISTICS OF THE ISOLATED PBL SUBPOPULATIONS ACCORDING TO PROLIFERATIVE RESPONSE TO MITOGENS

| PBL Subpopulations | Blastogenic Response to | |
|---|---|---|
| | PHA[a] cpm × $10^3/10^5$ cells | Con A[b] cpm × $10^3/10^5$ cells |
| Unseparated PBL | 168 | 211 |
| T-cells | 258 | 282 |
| B-cells | 6 | 4 |
| Monocytes | 4 | 7 |
| Reconstitution of T + B + Monocytes (7:2:1) | 215 | 216 |

[a]Maximum stimulation was at 0.3 μg/well
[b]Maximum stimulation was at 5 μg/well (G) Preparation of Antigen Antigen was prepared aseptically from fresh tissue from patients with invasive breast tumor cancer, benign breast tumors and other neoplasia. Fresh tissues from patients with breast carcinoma and benign breast disease were obtained from surgical specimens within 1 h of operation. After being trimmed free of fat and necrotic tissues, tumor specimens were cut up fine with scissors, passed through a steel mesh screen and treated with collagenase (2 mg per 1 gm tissue weight). The single cell suspension thus derived was washed twice with GNK to remove the enzyme and then homogenized in an ice-cooled nitrogen cavitation bomb at a pressure of 30 atmospheres for 15 minutes. The homogenate was centrifuged at $1000 \times g$ for 10 min at 4° C. to remove intact cells, nuclei and mitochondria. The supernatant was collected and re-centrifuged on a discontinuous sucrose gradient (from 40 to 60%) to isolate plasma membrane particulates. The interfacial band containing membrane antigen was obtained, its protein content determined, and adjusted to give final protein concentration of 2–5 mg/ml. This antigen preparation was stored in 0.5 ml volumes at −80° C. After thawing, the antigen preparation was always centrifuged at $2000 \times g$ for 10 min before being used.

(I) Assay $^{51}Cr$ labeled peripheral blood lymphocytes (PBL) in RPMI-1640+10% AB serum, or RPMI-1640±10% autologous serum at concentration of $1 \times 10^6$ cells/ml were used. Aliquots of 100 μl of the lymphocyte suspension containing $10^5$ cells were seeded in either glass culture tubes (Fisher, 13 mm × 100 mm) or polyethylene tissue culture tubes (NUNC, 13 mm × 100 mm) by use of a Hamilton dispenser. Equal volumes of normal or tumor antigen extracts in RPMI-1640 were added in an amount sufficient to provide 100 μg per tube. After mixing, the lymphocytes were incubated at 37° C. for 120 minutes in a humid atmosphere with 5% $CO_2$. Thereafter the tubes were removed, washed twice gently with 3 ml of GNK and inverted to drain on filter paper. The dried tubes were then counted for 1 min in a gamma counter. Tests were done in triplicate. At each experimental point a fourth tube was incubated in the usual manner. At the end of incubation the fourth tube was centrifuged at 800×g for 20 min. Supernatant was then removed and the free $^{51}$Cr determined. This represents the spontaneous release of $^{51}$Cr from the lymphocytes during the incubation.

Results (A) Identification of Reactive Cells in the LAI Reactions

Unseparated PBL and isolated subpopulations (T-, B-lymphocytes and monocytes) from normal subjects and Stage II breast cancer patients were incubated in AB serum plus breast tumor antigen, in AB serum plus benign breast tissue antigen (BBTA), and in AB serum plus unrelated tumor antigens: i.e. colorectal carcinoma, mesothelioma, acute myelocytic leukemia, stomach cancers, lung cancer and others. The recognition of these antigens as measured by the $^{51}$Cr LAI assay was shown in FIG. 5 and Tables III and IV.

antigen with significant reduction in adherence. The reactivity of T-lymphocytes was both specific and selective, as they did not respond to any other tumor antigens. Monocyte fractions on the other hand, responded to 3 out of the 4 unrelated tumor antigens tested. Isolated B-lymphocytes appeared not to be involved in recognition of tumor antigen.

In normal subjects tested, Table IV showed that unseparated PBL, T-lymphocytes and B-lymphocytes were all unreactive to tumor antigens. Isolated monocytes yielded non-specific TAT response against tumor antigens although the levels of reactivity were generally lower than those of cancer patients. The data appear to suggest that non-specific LAI response by monocytes is directed towards a surface antigen common to all neoplastic cells. Such non-specific response may be responsible for the occasional false positive observed in healthy subjects by previous LAI studies using PBL.

Figure 5:
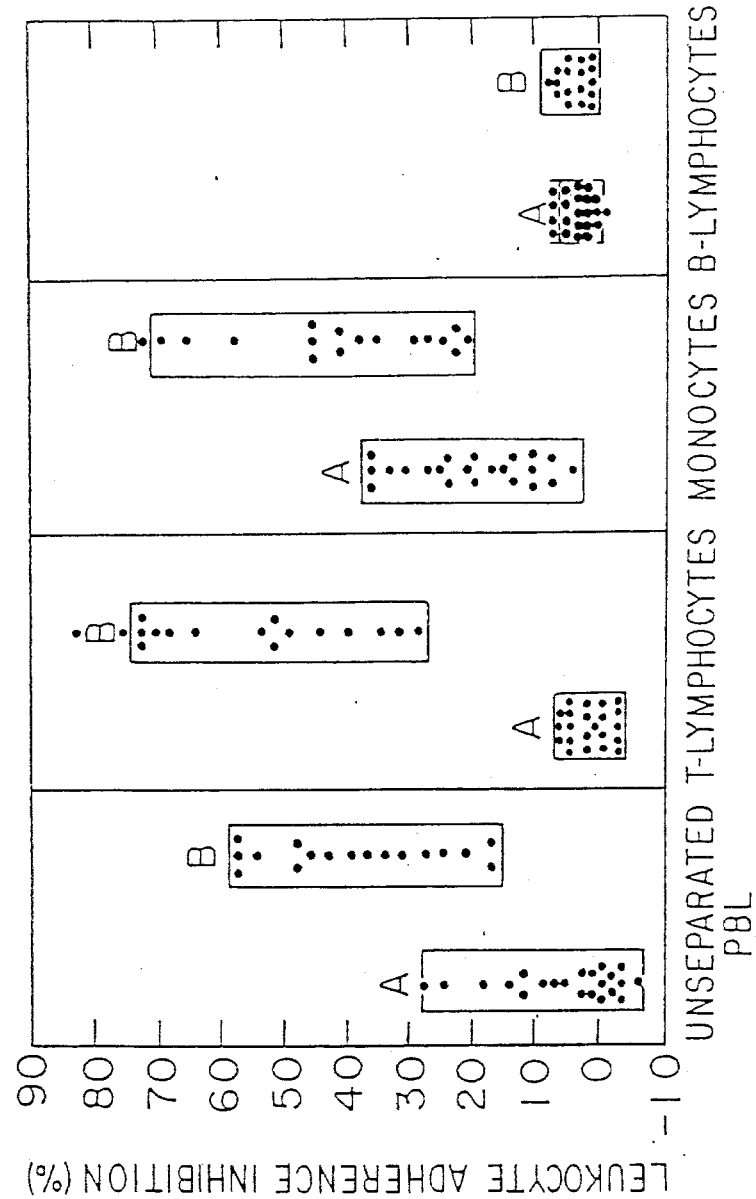

FIG. 5 shows the central role of T-lymphocytes in recognition of tumor antigen in the $^{51}$Cr LAI test. Compared to unseparated PBL, T-lymphocytes reflected the

TABLE III

CELLULAR RESPONSES IN PATIENTS WITH BREAST CANCER

| | Unseparated PBL LAI Index Mean ± S.D. (Range) | Purified PBL Subpopulations | | |
|---|---|---|---|---|
| | | T-Lymphocytes LAI Index Mean ± S.D. (Range) | Monocytes LAI Index Mean ± S.D. (Range) | B-Lymphocytes LAI Index Mean ± S.D. (Range) |
| Br. Ca Ag | 35.8 ± 13.8% (17–59%) | 53.4 ± 15.9% (30–74%) | 43.1 ± 16.5% (23–69%) | 3.3 ± 2.4% (0–1%) |
| Benign Breast Tumor Ag | 4.3 ± 3.8% (0–10%) | 1.75 ± 0.9 (0–3%) | 6.0 ± 2.7% (0–10%) | 7.3 ± 6.4% (0–14%) |
| Colorectal Ca Ag | 8.8 ± 4% (0–17%) | 8.3 ± 3.6% (0–12%) | 33.1 ± 14.6% (10–38%) | 2.8 ± 1.3% (0–4%) |
| Mesothelioma Ag. | 3.9 ± 1.9% (0–8%) | 4.8 ± 2.2% (0–6%) | 34.3 ± 16.4% (9–49%) | 7.6 ± 6.2% (0–17%) |
| Leukemic Ag | 11.3 ± 8.2% (0–26%) | 3.7 ± 2.8% (0–8%) | 13.5 ± 2.2% (12–15%) | 3.5 ± 1.5% (0–6%) |
| Stomach Ca Ag | 7.0 ± 2.4% (0–10%) | 3.1 ± 2.2% (0–6%) | 37.25 ± 15.5% (24–56%) | 5.0 ± 4.2% (0–10%) |

TABLE IV

CELLULAR RESPONSES IN NORMAL SUBJECTS

| | Unseparated PBL LAI Index Mean + S.D. (Range) | Purified PBL Subpopulations | | |
|---|---|---|---|---|
| | | T-Lymphocytes LAI Index Mean ± S.D. (Range) | Monocytes LAI Index Mean ± S.D. (Range) | B-Lymphocytes LAI Index Mean + S.D. (Range) |
| Br. Ca Ag | 9.3 ± 8.9% (0–30%) | 4.7 ± 8% (0–7%) | 22.6 ± 14.3% (7–39%) | 2.7 ± 2.0% (0–5%) |
| Benign Breast Tumor Ag | 7.7 ± 4.3% (0–19%) | 3.0 ± 2.6% (0–7%) | 10.7 ± 6.4% (0–20%) | 2.7 ± 2.1% (0–6%) |
| Colorectal Ca Ag | 5.7 ± 2.3% (0–9%) | 6.2 ± 3.4% (0–14%) | 15.8 ± 8.2% (0–26%) | 4.7 ± 3.2% (0–13%) |
| Mesothelioma | 2.5 ± 1.3% (0–14%) | 1.9 ± 1.7% (1–4%) | 11.3 ± 8.4% (5–18%) | 4.3 ± 3.5% (0–11%) |
| Leukemic Ag | 2.8 ± 0.9% (0–4%) | 1.7 ± 2.0% (1–4%) | 8.8 ± 6.1% (3–14%) | 3.1 ± 2.4% (0–5%) |
| Stomach Ca Ag | 4.8 ± 3.5% (0–10%) | 5.5 ± 3.6% (0–16%) | 2.7 ± 0.6% (0–4%) | 2.0 ± 1.0% (0–3%) |

In breast cancer patients (Table III) unseparated PBL in response to breast tumor antigens showed leukocyte adherence inhibition ranging from 17 to 59% (mean 35.8%). These unseparated leukocytes were not responsive to BBTA and unrelated tumor antigens (mean LAI index less than 12%). On comparing the reactivity of various isolated leukocyte subpopulations from these breast cancer patients, significant differences in response to tumor antigens were observed. Both T-lymphocytes and monocytes responded to breast cancer antigen with significant reduction in adherence. The LAI reactivity of breast cancer patients with higher frequency and remarkable specificity (LAI index of 30 to 73%). From the data presented here, a positive response was defined as one that showed greater than 20% inhibition of adherence. Such interpretation allowed clear cut and accurate prediction of malignancy in all breast cancer T-lymphocyte subpopulations studied. With unseparated PBL of the same study subjects, 2 out of 10 yielded 20% as LAI. In light of these new findings, we concluded that in order to achieve the desired specificity, isolated T-lymphocytes from the cancer patients' PBL must be used for the proper performance of the $^{51}$Cr LAI tests.

(B) Clinical Studies in Pre-operative Cancer Patients

Blood samples were drawn prior to breast biopsy from 46 patients suspected of breast lesions, benign or malignant. Control subjects consisted of 32 healthy normal female subjects and 15 patients with acute myelocytic anemia (AML) in complete clincal remission.

Figure 6:
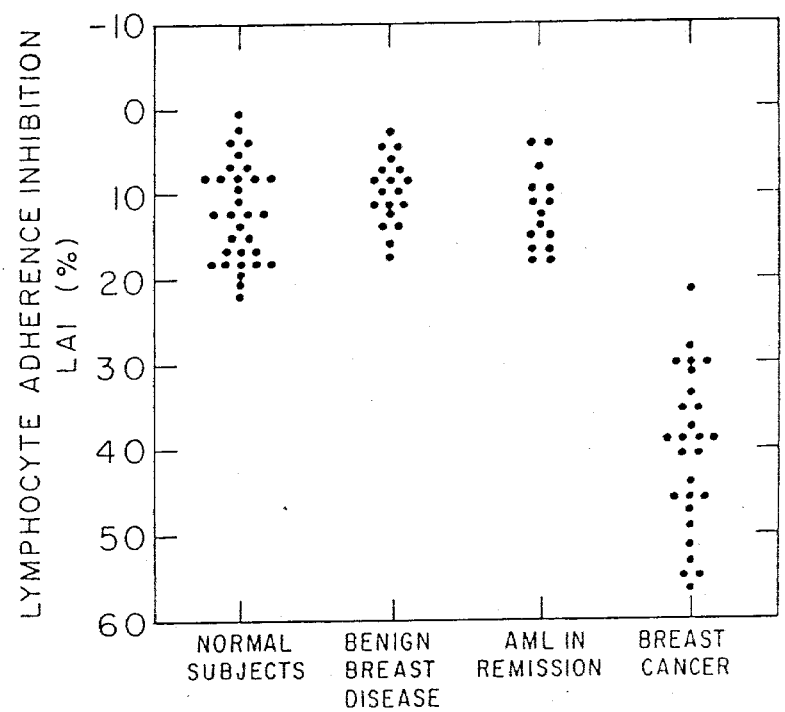

Incubations were all performed in the presence of 10% normal AB serum. Results summarized in FIG. 6 show that unseparated PBL obtained from the 46 patients subjected to breast biopsies can be classified into two groups according to their response to breast cancer antigens in the $^{51}$Cr LAI assay. A group of 27 patients showed strong leukocyte adherence inhibition, ranging from 27 to 56%, mean 42.04±9.28%, as a response to breast tumor antigen. These same patients' PBL incubated in the presence of benign breast tissue antigen showed LAI of 0–10%. All 27 cases were subsequently confirmed by histopathology to have cancer of the breast, Stages I and II.

On the other hand, 19 of the women with breast masses showed poor response to breast cancer antigen with LAI values ranging from 3 to 18%; they were equally unresponsive to benign breast tissue extract (range 0–15%). These 19 patients were diagnosed to have benign breast lesions.

(C) Advanced Breast Carcinoma

Figure 7:
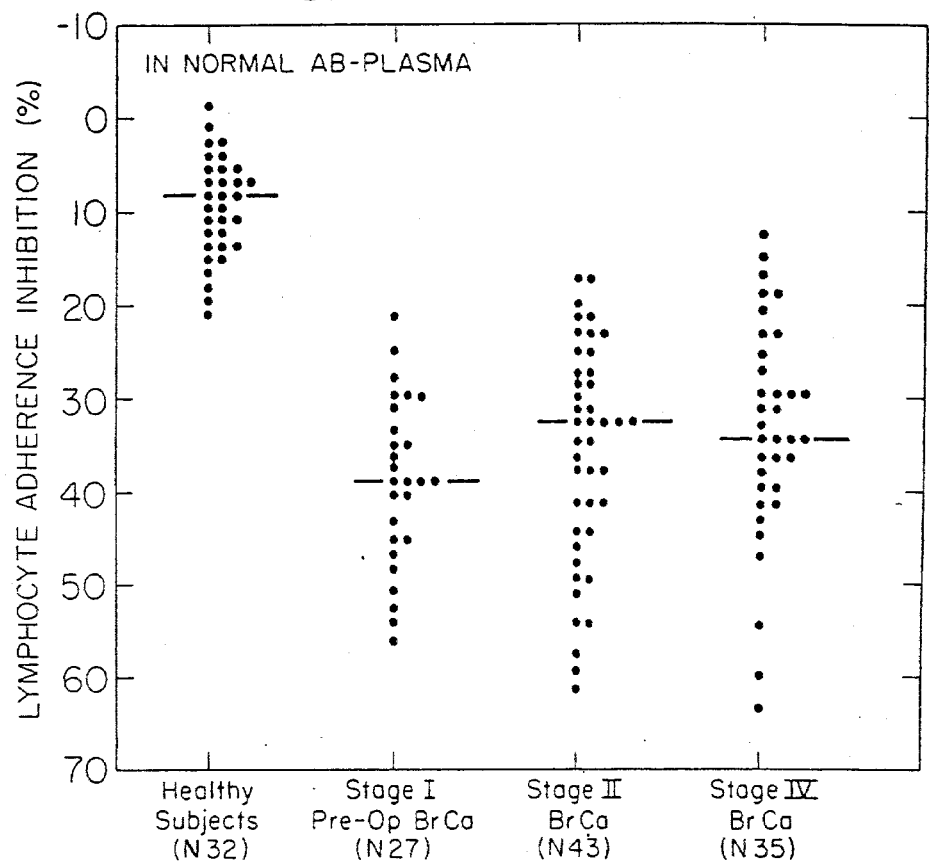

Results in pre operative Stage I and II breast cancer patients conclusively demonstrated the expression of specific cell-mediated immunity in subjects with small tumors in the presence of normal AB serum. After mastectomy LAI was positive in metastatic and recurrent cancer as well as in patients with no residual tumor. For further evaluation of this specificity and the effect of tumor burden on tumor host relationship, LAI testing was expanded to include patients with more advanced breast cancer. The response to breast tumor antigens by the unseparated PBL of three groups of breast cancer patients at various clinical stages of the neoplasm in the presence of normal AB serum was summarized in FIG. 7. The groups studied include patients who had clinically localized disease to the breast alone (Stage I), patients with localized neoplasm to the breast and axillary lymph nodes (Stage II) and individuals with widespread metastasis (Stage IV). The results show no statistical difference between LAI response and the clinical status (tumor burden) of these breast cancer patients.

Figure 8:
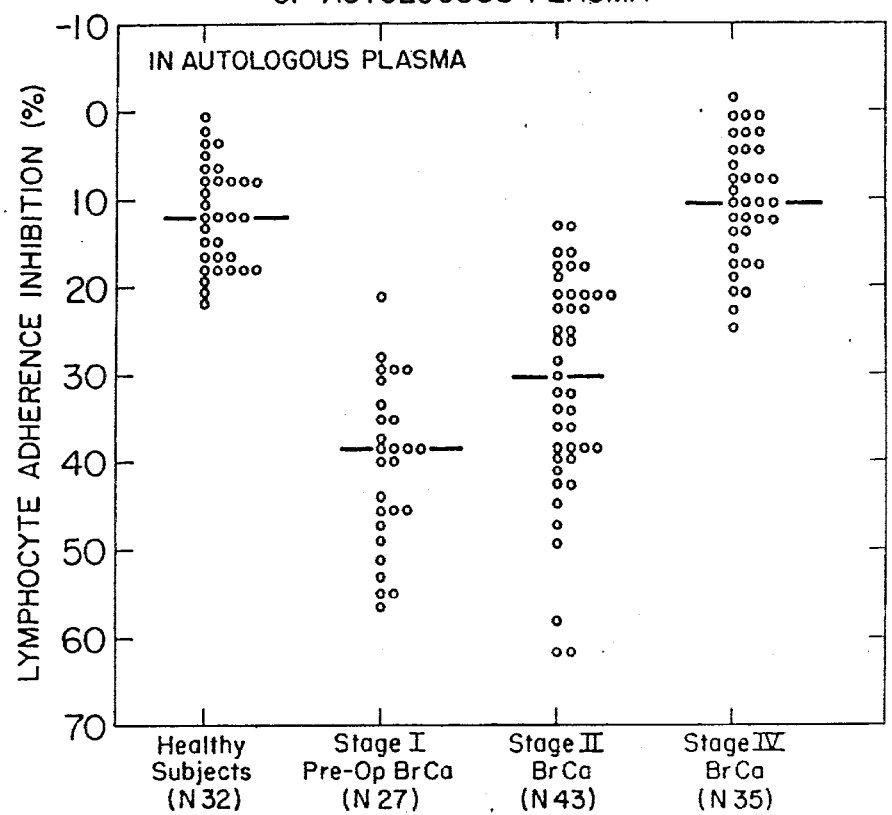

As shown in FIG. 8, and in Table VII, in subject with Stage I and II breast cancer, no abolition of cell mediated immunity by the patients' own sera was found. The mean LAI index was 39.6 for Stage I and 30.3±6% for Stage II in autologous sera compared with 41.2±6% and 34.4±5% in the presence of normal AB plasma. By contrast patients with Stage IV breast cancer (31 out of 35 patients) showed reduced recognition of breast tumor antigen in the presence of autologous serum from 38.2±5% to 10.835 5%.

(D) Optimum Labeling Conditions

To test the optimum labeling conditions, peripheral blood leukocytes were suspended in polyallomer tubes (Beckman) in one of the following media:

RPMI-1640 (A); 0.9% sodium chloride (B); 0.9% sodium chloride+1 g/l glucose (C); 0.9% sodium chloride+4 g/l KCL (D); 0.9% sodium chloride+2 g/l KCL+1 g/l glucose (E); 0.9% sodium chloride+4 g/l KCL+1 g/l KCL (F); and 0.9% sodium chloride+6 g/l KCL plus 1 g/l glucose (G). $^{51}$Cr sodium chromate with specific activity of 300–500 µCi/µg was used throughout this study. The final lymphocyte concentration was between 0.5 and $2 \times 10^7$ cells/ml. After incubation, at 37° C. for 45 minutes as described above, labeled lymphocytes were washed, resuspended in RPMI-1640 at $1 \times 10^6$ cells/ml, and 100 µl of cell suspension was counted. Media A, B, C and D failed to yield label PBL having an intracellular radioactivity of 10,000 per $10^5$ PBL or higher. Media E, F and G all yielded labeled PBL preferred for use in the preferred embodiment of this invention, with activity of up to $20 \times 10^3$ per $10^5$ cells being obtained.

(E) Optimal Incubation Time and Number of Leukocytes

Labeled PBL obtained from breast cancer patients using lymphocyte concentrations from $1 \times 10^3$ to $5 \times 10^5$ per ml were incubated in RPMI-1640 containing 10% AB serum and 100 µg/tube of breast cancer or normal breast antigens. At predetermined periods of time, incubation was stopped and the radioactivity of adherent cells was determined. FIG. 8A shows that a plateau was reached after 120 min incubation with either BBTA or breast cancer antigens. Longer incubation than 120 min did not further alter the LAI values.

Using the 120 min incubation interval, there was a direct linear relationship between the number of cells seeded in the assay tube and the number of adherent cells observed (FIG. 8B). In tubes seeded with $1 \times 10^5$ cells, the baseline value of adherence in 10% AB serum without tumor antigens was 48±7%, the mean cpm being 14,900 cpm before incubation and 7,100 cpm afterwards. When 100 µg of tumor antigen were added to the mixture, the mean radioactivity after incubation was 4615 cpm, i.e., an LAI index of 31±8% In comparison, tubes with only $10^4$ cells in 10% AB serum without antigen had radioactivity of 1,500 cpm before incubation and 700 cpm afterwards. The same correlation was observed on addition of 100 µg of tumor antigen; the adherent radioactivity and and LAI index being 462 cpm and 31% respectively. These observations were not surprising since the surface area of the bottom of each tube, estimated to be $4.5 \times 10^8$ µm$^2$, should accommodate $3.9 \times 10^7$ adherent lymphocytes before saturation. Thus within the range tested the number of lymphocytes used should not alter the $^{51}$Cr-LAI assay values.

(F) Effect of Different Types of Culture Tubes in Performance of LAI

Triplicate samples of labeled lymphocytes ($1 \times 10^5$) from 10 normal subjects in 200 µl of RPMI-1640 containing 10% AB serum and 100 µg benign breast tissue extract were incubated in either borosilicate glass culture tubes (Fisher) or polystyrene tissue culture tubes (NUNC No. 30201) for 2 h and the percent adherent cells was determined. Since there was no significant difference between the mean percent adherence indexes using either glass or polystyrene tubes (P< <0.05) and the data were perfectly correlated (r=1.0), polystyrene tubes were used in all subsequent experiments because they are more resistant to breakage.

DISCUSSION

The LAI assays are potentially suitable as an investigatory tool for detection of cell-mediated immunity and serum blocking in evaluation of immunocompetence, residual tumor burden and therapeutic effects in cancer patients.

Applying a new radioisotopic LAI assay we have established the central role of T-lymphocytes both as indicator and as responder cells in the LAI response.

Several novel approaches were taken. The first is the pre-labeling of unseparated PBL prior to isolation and characterization. At the end of separation, all cell subpopulations uniformly retained the majority of the Cr-isotope incorporated. This allows their subsequent use in the $^{51}$Cr-LAI assay and results in more objective and quantitative monitoring of adherence pattern than was ever possible in other methods involving visual counting. Another unique feature in the experimental design is the use of E-rosette sedimentation followed by Percoll gradient separation in a two-stage isolation procedure. Applying this new combination of techniques, over 85% of the T- and B-lymphocytes and monocytes can be recovered from the same initial population of cells. Besides providing higher yield, this procedure has other important features. Pretreatment of the E with AET stabilizes the rosettes by creating a more effective interaction between E and T-lymphocytes. The rosettes are not as fragile as with untreated E, thereby facilitating handling and increasing purity in separation. The T-enriched populations thus obtained were homogeneous both by surface markers and functional criteria. They responded to T-cell mitogens by proliferating (69% increase as compared to the unseparated cells).

The non-rosetting cells contained a mixture of B-cells and monocytes. Monocytes were removed by Percoll gradient separation. This method for isolating monocytes is preferable to other commonly employed methods based on "differential adherence" such as Sephadex G10 columns, glass beads on nylon wool. It is well known that adherence and mechanical detachment of monocytes by procedures activate these cells and cause irreversible damages. The negative separation technique by Percoll gradient centrifugation avoids such activation. The bottom layer in the Percoll gradient consists mainly of B-lymphocytes and null cells. By use of the EAC rosetting techniques B-lymphocytes can be removed from null cells which have neither E or $C_3$ receptors. The B-lymphocyte enriched fractions thus obtained were all homogeneous by surface markers and functional criteria. The enriched PBL subpopulations were applied in the $^{51}$Cr LAI assay under different incubating conditions.

The identity of reactive cells that undergo reduction in adherence as a specific response to tumor antigen was next investigated. In patients with invasive cancer, reduction in adherence was manifested by both T-lymphocytes and monocytes. However, tumor specific LAI response to antigen of the same tumor type was observed only with T-lymphocytes. These results indicate that T-lymphocytes upon sensitization with homologous tumor antigen secrete a lymphokine that in turn affects their own adherence. Such lymphokines, when properly identified, will enable us to utilize other procedures, i.e. enzyme-linked immunosorbent assays, radioimmunoassay, immunofluorescence and monoclonal antibodies, etc., in diagnosis of neoplastic diseases and in monitoring patients' response during treatments.

Figure 3:
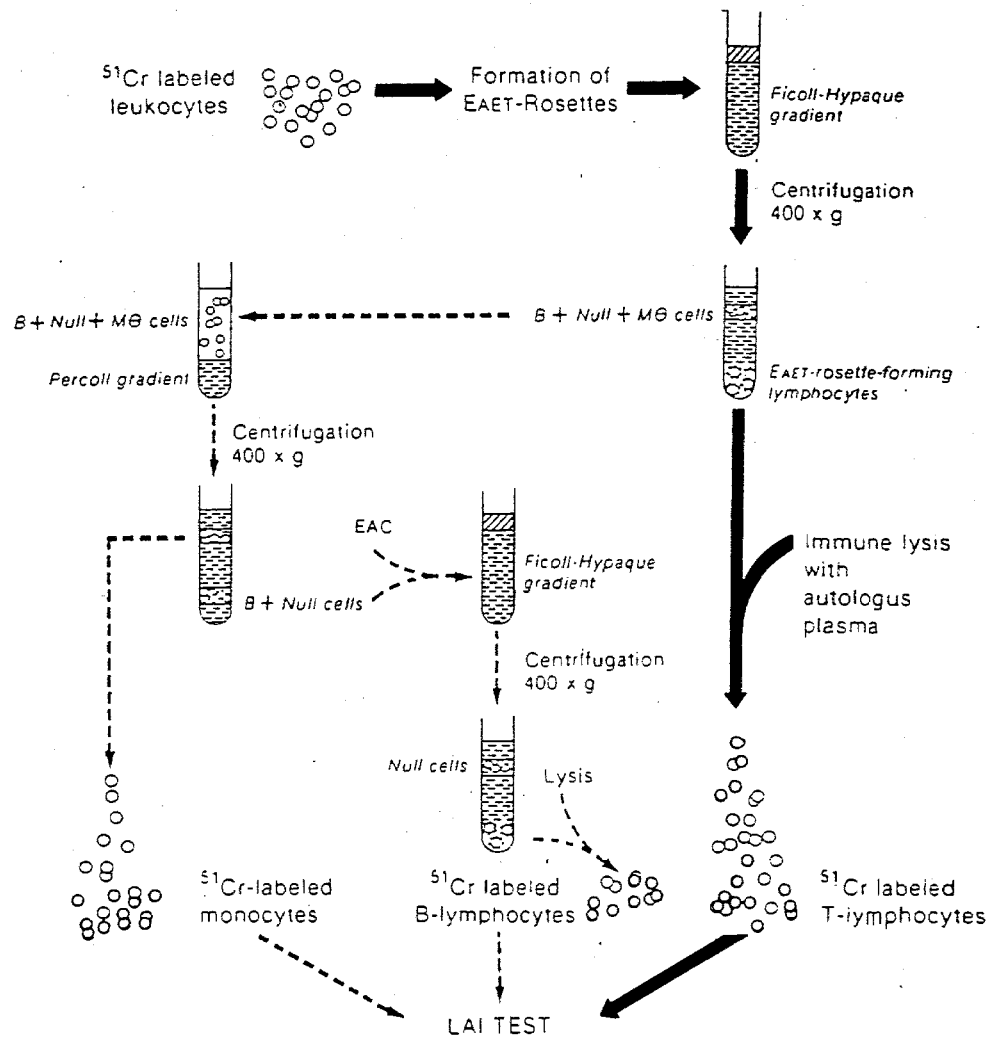

In light of our studies of T-cells, B-cells and monocytes in the LAI assay, we conclude that in the LAI response two immunological reactions involving different leukocyte subpopulations occur simultaneously. The primary interaction of TSTA with sensitized T-lymphocytes elicits the tumor-specific LAI response observed in cancer patients. In addition, there is a non-specific response to a common neoantigen (possibly CEA) by both sensitized and non-sensitized monocytes, which has resulted in the occasional false positive LAI reactions observed in some healthy subjects. In light of our discoveries, we conclude that where a tumor-specific reaction is desired in the LAI, monocytes should be removed from the incubation mixtures and purified T-lymphocytes should be used. In our ongoing clinical studies, the pathway depicted by heavy arrows in FIG. 3 are followed routinely. On the other hand, where the identity of the tumor is unkown or uncertain, monocytes, because of their non-specific response, can be used in the LAI assay to ascertain whether the patient appears to have a neoplastic disease whose location should be more specifically investigated.

The predictive and discriminatory power of this new invention may be gauged from the results of our clinical studies in pre-and post-operative cancer patients. $^{51}$Cr LAI assay performed on isolated T-lymphocytes in normal AB human serum was able to discriminate between human tumors of different histological types or sites of origin. All patients with tumors other than the specific types assayed gave a negative LAI reaction to that particular tumor antigen. In double blind studies in pre-operative patients, clear and accurate prediction of the presence of cancer was achieved. The new invention was able to distinguish effectively between patients with carcinoma in its early stages from those with benign diseases. Upon addition of autologous serum, humoral blocking factors present in serum of patients with advanced tumor bind to the membrane of T-lymphocytes and block the subsequent interaction between tumor antigen and specific membrane receptor. Specific serum factor(s) were found in almost all patients with advanced cancer.

Applying the $^{51}$Cr LAI assay on isolated T-lymphocytes we are able to monitor simultaneously CMI and serum blocking activity. The LAI reaction was shown to demonstrate both a specific lymphocyte-mediated response to TSTA and a non-specific reaction by the monocytes to a common neoantigen (possibly CEA). This new invention is able, therefore, to dissect the various components of anti-tumor immunity and thus offer unlimited possibilities and applications in cancer research.

We claim:

1. A method of preparing radio-labeled leukocytes comprising incubating said leukocytes in an incubating medium containing a nutrient sugar, a physiologically acceptable concentration of sodium chloride and from 1 to 6 gm/liter by weight, based on the volume of said incubation medium, of potassium chloride, said incubating medium further containing an amount of radioactive chromium ($^{51}$Cr) effective to impart radioactivity to said leukocytes, and continuing the incubation for a period of time sufficient for the leukocytes to absorb radioactive chromium in an amount sufficient that the radio-labelled leukocytes exhibit a radioactivity of at least $10 \times 10^3$ counts per minute per $10^5$ cells.

* * * * *